(12) United States Patent
Joseph

(10) Patent No.: US 6,306,094 B1
(45) Date of Patent: Oct. 23, 2001

(54) INSTRUMENT HAVING ENHANCED ULTRASOUND VISIBILITY

(75) Inventor: Anton Emmanuel Arulraj Joseph, Wallington (GB)

(73) Assignee: BTG International Limited, London (GB)

(*) Notice: Subject to any disclaimer, the term of this patent is extended or adjusted under 35 U.S.C. 154(b) by 0 days.

(21) Appl. No.: 09/301,618

(22) Filed: Apr. 29, 1999

Related U.S. Application Data

(63) Continuation of application No. PCT/GB97/02935, filed on Oct. 24, 1997.

(30) Foreign Application Priority Data

Oct. 31, 1996 (GB) .................................................. 9622711

(51) Int. Cl.$^7$ ...................................................... A61B 8/00
(52) U.S. Cl. ........................................... 600/458; 600/459
(58) Field of Search ............................... 600/458, 466, 600/467, 471, 437, 459; 424/9.52

(56) References Cited

U.S. PATENT DOCUMENTS

| | | |
|---|---|---|
| 4,407,294 | 10/1983 | Vilkomerson . |
| 4,582,061 | 4/1986 | Fry . |
| 5,081,997 | 1/1992 | Bosley, Jr. et al. . |
| 5,127,945 | 7/1992 | Miller . |
| 5,373,845 | * 12/1994 | Gardineer et al. ............. 600/458 |
| 5,536,489 | 7/1996 | Lohrmann et al. . |
| 5,782,764 | * 7/1998 | Werne ......................... 600/411 |
| 5,795,562 | * 8/1998 | Klaveness et al. ............. 424/9.52 |
| 6,047,218 | * 4/2000 | Whayne et al. ................ 600/458 |

FOREIGN PATENT DOCUMENTS

| | | |
|---|---|---|
| 0 624 342 A1 | 11/1994 | (EP) . |
| 93/00930 | 1/1993 | (WO) . |
| 94/03110 | 2/1994 | (WO) . |
| 94/21302 | 9/1994 | (WO) . |

OTHER PUBLICATIONS

Miller, J.E., Derwent Acc. No. 92–249311/30, "Effervescent tablet for use . . . ".
USP Abstract No. 4805628, Fry et al, "Ultrasound contrast media . . . ," (1989).
USP Abstract No. 5490521, Davis et al, "Ultrasound biopsy needle" (1996).
USP Abstract No. 4,869259, Elkins, D.J., Echogenically enhanced surgical . . . ) (1989).

* cited by examiner

*Primary Examiner*—Brian L. Casler
*Assistant Examiner*—Maulin Patel
(74) *Attorney, Agent, or Firm*—Nixon & Vanderhye

(57) ABSTRACT

An instrument (10) for ultrasonic imaging comprises a probe (12) for insertion into a material (62) containing a liquid. The probe (12) has a coating comprising a carrier material (30) and a quantity of reactive material (32) which, upon contacting a reactant produce a quantity of bubbles (62) adjacent the coating for reflecting ultrasonic energy. In one application the probe (12) comprises a biopsy needle and the coating is positioned towards a sharp distal end thereof (14a) thereby to facilitate the guiding and positioning thereof. Alternatively, the coating can be provided along the entire length of the instrument (10) or at descrete portions along its length.

25 Claims, 3 Drawing Sheets

INSTRUMENT HAVING ENHANCED ULTRASOUND VISIBILITY

This is a continuation of PCT application PCT/GB97/02935, filed Oct. 24, 1997.

The present invention relates to instruments suitable for use in procedures involving ultrasound imaging and more particularly to such an instrument having a means capable of generating an enhanced reflected ultrasound signal.

Ultrasound imaging apparatus include a transducer operative to both emit and receive ultrasound energy. Such transducers are typically held against the skin of a patient and emits ultrasound energy thereinto. A portion of the emitted ultrasound energy is reflected back from body structures and is received by the transducer. Reflected ultrasound is converted into electrical signals which are then transmitted to a signal processor and then displayed on a monitor thereby to create a real-time video image of the body parts from which the ultrasound energy has been reflected.

Some medical procedures require one to obtain tissue samples for diagnosis. Typically, such samples are obtained by inserting a long biopsy needle, or the like, into the area of interest and observing the needle positioning via the video image of the needle and its surroundings. Such a needle includes a sharp tip which, in operation, cuts into the tissue under investigation.

Unfortunately, the above-mentioned medical procedures may be difficult to perform due to the poor sonar reflectivity of presently known instruments used during such procedures. One possible solution to this problem is presented in EP-A-624 341 in which there is described a medical instrument having an enhanced ultrasonic visibility. The instrument comprises a probe or needle for insertion into a patient and is provided at selected locations with deposits of a material comprising a matrix of gas bubbles constrained within a polymeric material. The bubbles exhibit a high degree of ultrasonic reflectivity and help enhance the ultrasonic image.

An alternative arrangement is described in U.S. Pat. No. 5,081,997 in which an echogenic medical device for insertion into a patient is provided with a portion having an acoustic impedance different from that of the surrounding medium thereby to provide an enhanced ultrasonic image. The portion may, for example, be formed of partially spherical indentations or glass micro spheres. Again the highly reflective portion is provided at a critical position, such as the needle tip, so as to assist the operator in guiding the instrument.

Tests have shown that, in certain circumstances, the above-mentioned arrangements do not adequately improve the ultrasonic image available to the operator. Consequently, there still exists a requirement for an instrument for use during ultrasound imaging procedures which significantly enhances the ultrasonic image available to the operator. The present invention aims to meet this requirement by providing such an instrument with a means of creating a plurality of fine mobile gas bubbles adjacent said region. Such fine gas bubbles being mobile are easily detected by an ultrasound apparatus and significantly enhance the ultrasound image of the instrument. Mobility may be as a result of bubble migration or a change in size.

Accordingly, the present invention provides an instrument insertable into a medium and capable of being detected with sonic imaging equipment comprises:

an elongate member, for insertion into said medium and having a region the position of which it is desirable to monitor; and bubble generating means, for generating a plurality of discrete mobile bubbles at said desired region, whereby said discrete mobile bubbles are detectable by sonic imaging equipment thereby to give an accurate indication of the position of said region.

In another embodiment of the present invention there is provided a method of determining the position of an instrument including the steps of:

(a) inserting the instrument into a material;

(b) creating a plurality of discrete mobile bubbles at the desired region; and (c) positioning an ultrasound transducer on a surface of the material and transmitting an ultrasonic signal in a direction substantially towards said instrument thereby to cause at least some of said signals to be reflected by said bubbles and collecting said reflected signal in said transducer;

(d) converting the reflected ultrasound signal into an electrical signal suitable for creating a display on a video monitor; and (e) displaying a video image from said signal, thereby to provide a visual representation of the position of said instrument.

The present insertion will now be more particularly described by way of example only with reference to the following drawings in which.

Figure 2:
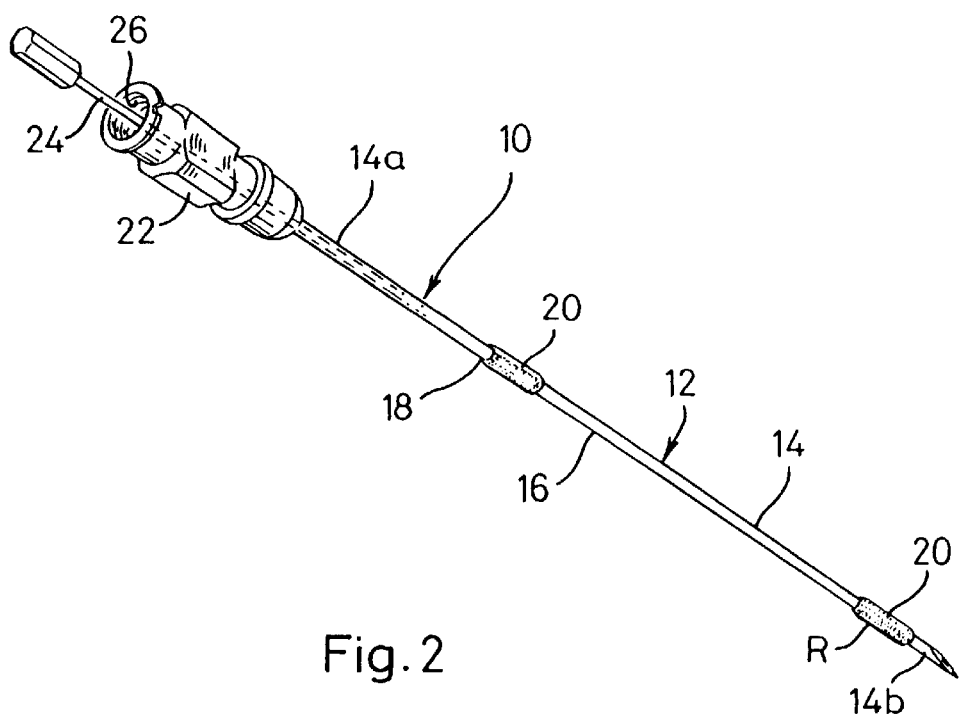
FIG. 2 is a perspective view of a biopsy needle in accordance with the present invention.
Figure 3:
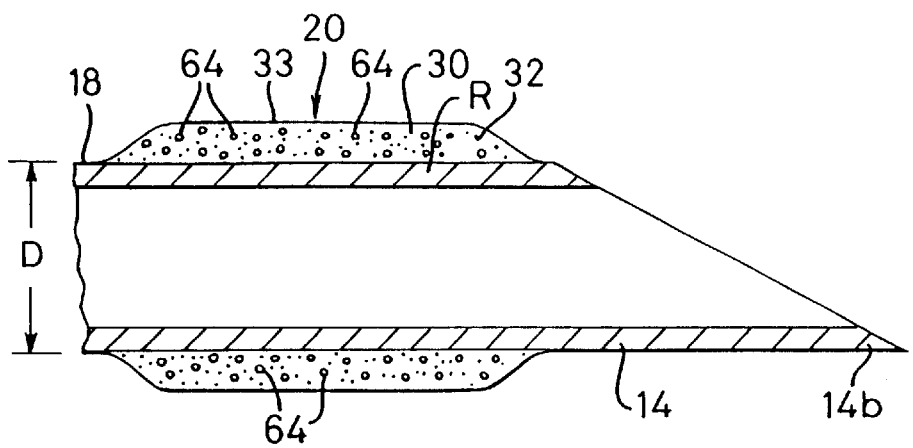
FIG. 3 is an enlarged cross-sectional view of a portion of the needle shown in FIG. 2.

Referring now to the drawings in general but particularly to FIGS. 2 and 3, a medical instrument 10 in the form of, for example, biopsy needle 12 comprises an elongate needle 14 having proximal and distal ends 14a, 14b, the latter of which is sharply pointed. A cylindrical lumen 16 extends between the ends and provides a substantially smooth exterior surface 18 having one or more regions R upon which is deposited a coating 20, the function of which will be described in detail later herein. The needle 12 also includes a mounting 22 generally of a plastics material which surrounds and is secured to the proximal end. A stylet 24 is slidably and removably disposed within the lumen 16 and substantially blocks the distal end 14b and helps form a cutting edge for use during the insertion process. When removed the stylet 24 exposes a threaded or ribbed portion 26 on mounting 22 onto which a hypodermic syringe may be removably secured and used in a manner well known and therefore not described further herein.

The biopsy needle of the present invention is characterised in that the one or more regions R are provided with a coating 20 in which are generated a plurality of mobile gas bubbles each of which has a high degree of ultrasonic reflectivity. FIG. 3 for example shows coating 20 positioned towards the distal end 14b of needle 12 which assists the accurate positioning of the end in a manner to be described in detail later herein. Other positions may however be used to advantage and the distance between regions of deposited coatings 20 may be preset thereby to assist in determining how deep the instrument has been inserted. Alternatively, when it is desirable to monotor the position of the entire needle, the coating may be provided along the entire length of the needle. The deposited coating 20 itself comprises a carrier material 30 and means for generating a plurality of very fine mobile gas bubbles. The function of the carrier material is to provide a matrix or support site for the bubble generating means which can take any one of a number of forms, two of which are detailed below. In essence, the bubble generating means comprises a reactive substance which, upon interaction with a reactant, acts to produce the required bubbles. A secondary function of the carrier material 30 is to provide a bulk of material which affords mobility of the bubbles to facilitates ultrasonic detection thereof. For enhanced performance, the carrier material is chosen so as to have an ultrasonic impedance the same as or close to that of the material into which it is to be inserted. By matching the impedance in this manner, it is possible to reduce the reflections at the interface between the carrier material and the material in which it is inserted and increase the quantity of ultrasound interacting with the bubbles. Clearly, any such increase will enhance the quality of any reflected ultrasound signal.

In one arrangement the carrier material 30 is used to support a quantity of effervescent material 32 (the reactive substance) which, upon contacting a liquid (the reactant), effervesces thereby to produce a quantity of mobile bubbles 64 which are highly reflective of ultrasonic energy. These bubbles are mobile in two senses. Firstly, they are mobile in the sense that they are able to migrate through the material and, secondly, they are mobile in the sense that they grow in size as they develop. Typically a bubble generated in this manner will grow into a bubble having a diameter of at least 5 microns and probably more. The carrier material 30 also acts to protect the effervescent material 32 which tends to be less robust and hence susceptible to damage during handling. In a preferred arrangement the carrier material comprises a hydrophilic material the advantages and function of which will be described later herein. Whilst it will be appreciated that any one of a number of materials could be employed to perform the function of the carrier material, it has been found that epoxy based resins are particularly suitable for such applications. Such materials can be applied by a simple dipping technique followed by a curing step and are highly bio-compatible should the needle be required for use on a human or animal patient. A particularly suitable material is EPOTEX (Trade Mark) epoxy 353 ND resin which is typically cured by heating at 80° C. for 30 minutes. Polymers having a plurality of interconnecting pores are well known to those skilled in the art and can be "engineered" to create a pore structure suitable for a particular application. Clearly, such materials lend themselves to use in the present invention in which it is desirable to produce an open cellular structure through which generated bubbles are able to pass. Polyolefins such as polyethylene or polypropylene are examples of such materials. Alternatively, one might use polystyrene which, whilst normally being hydrophobic, can be manufactured in hydrophilic form. The effervescent material chosen may comprises a mixture of sodium hydrogen carbonate and citric powder. Such a material is highly bio-compatible and therefore presents little if any problem when the needle is employed for use on a human or animal. Other materials may be employed, particularly when bio-compatibility is not a problem. The preferred form of effervescent material was created by mixing equal amounts of the two components which was then added in a 3:7 ratio to the epoxy carrier 30 and throughly mixed before being applied to the needle and cured at the above-mentioned temperature. Other ratios of mix are possible depending upon the performance requirements of the final product.

In an alternative form, the reactive substance may be one which generates a plurality of bubbles when exposed to a particular temperature. Examples of such materials are: peroxide compounds, which give off oxygen and water when heated and diamene compounds which give off nitrogen when heated. Clearly, such compounds might not lend themselves for use in living patients but are certainly suitable for use in industrial applications.

Figure 4:
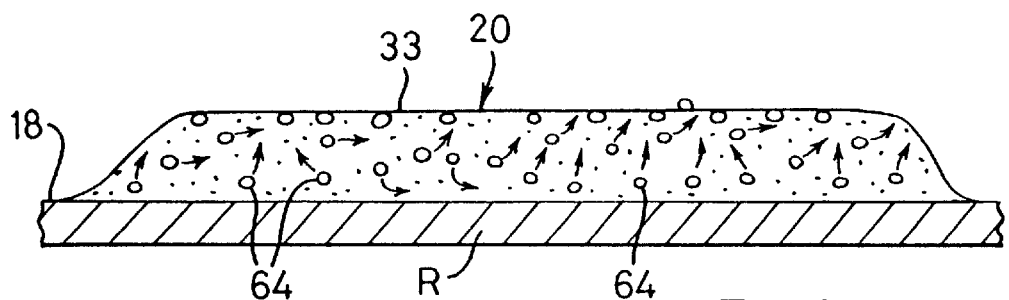
FIGS. 4 to 6 are enlarged cross-sectional views of various forms of the present invention.
Figure 5:
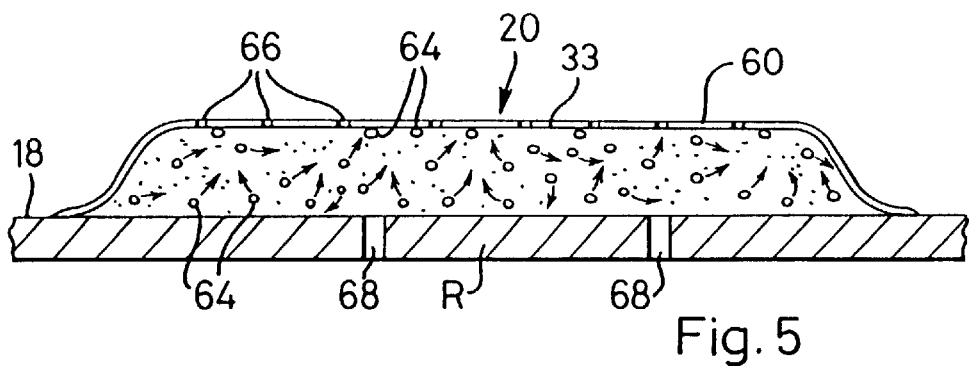
Figure 6:
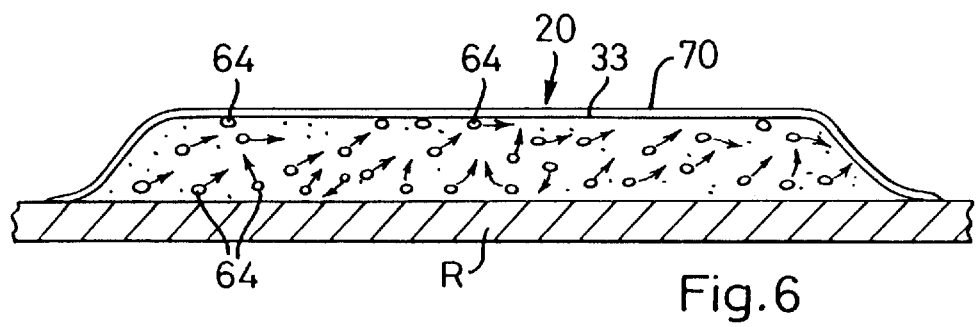

In some situations it will be desirable to ensure any generated gas bubbles are retained in the carrier material and do not enter the material into which the instrument has been inserted. This requirement can be met by employing an outer layer 60 of gas impermeable material and enveloping, or substantially enveloping, the carrier material 30 as shown in FIG. 5. If such an arrangement is used in conjunction with a bubble generating means requiring interaction with a fluid source it will be necessary to provide some form of opening in the layer 60 or in the needle itself, as shown at 66 and 68. The size and number of such openings need not be substantial as only a relatively small amount of fluid need be passed into the carrier material in order to initiate the reaction which produces the desired bubbles. By limiting the number and size of the openings it will be possible to severely limit the quantity of bubbles escaping as such bubbles must pass through the openings against the action of incoming fluid and against any pressure being generated by the surrounding material. Alternatively, one can employ a layer which is impermeable to gas but permeable to the fluid being employed to create the reaction as shown at 70 in FIG. 6. In many applications it will be possible to dispense with the layer and just modify the structure of the carrier material 30 such that it performs the same function. For example, the pore size may be selected such that it allows the fluid to permeate thereinto but is sufficiently small as to act to retain any bubbles once they reach a predetermined size. This arrangement is shown in FIG. 4 and has the advantage of allowing a certain degree of bubble mobility within the carrier material whilst minimising the loss therefrom. Any gas bubbles which do make it to the interface with the surrounding material will experience difficulty in breaking free of the carrier material and migrating into the surrounding material. Alternatively, where migration into the surrounding tissue is not a problem, one could employ a much simpler arrangement in which the pore size is such as to not prevent migration.

Referring now once again to FIG. 3 it will be appreciated that, once mixed, the coating may be applied to any region of the needle 14 by dipping, spraying or painting techniques. The particular arrangements of FIG. 3 illustrates a coating applied towards the distal end 14b of the needle so as to facilitate the guiding and positioning of the sharp tip during insertion into the material under investigation. Any outer layer 60 may be applied in a similar manner.

The above-mentioned needle is employed in conjunction with a conventional ultrasound imaging apparatus well known to those skilled in the art and therefore not described in detail herein. The essential components of such a device are however shown in FIG. 1 and include an ultrasound generator/receiver 52, signal processing means 54 for converting a received ultrasound signal into an electrical signal suitable for creating a display on a video monitor and a video monitor 56 for displaying said display.

Figure 1:
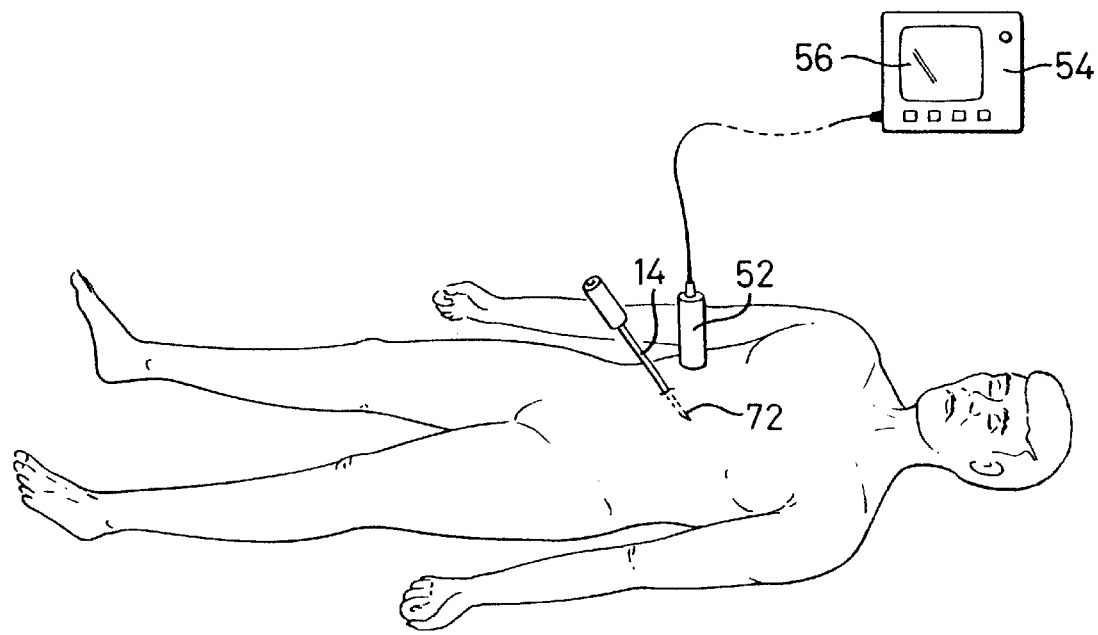
FIG. 1 is a general view of the present invention being used on a patient.
Figure 7:
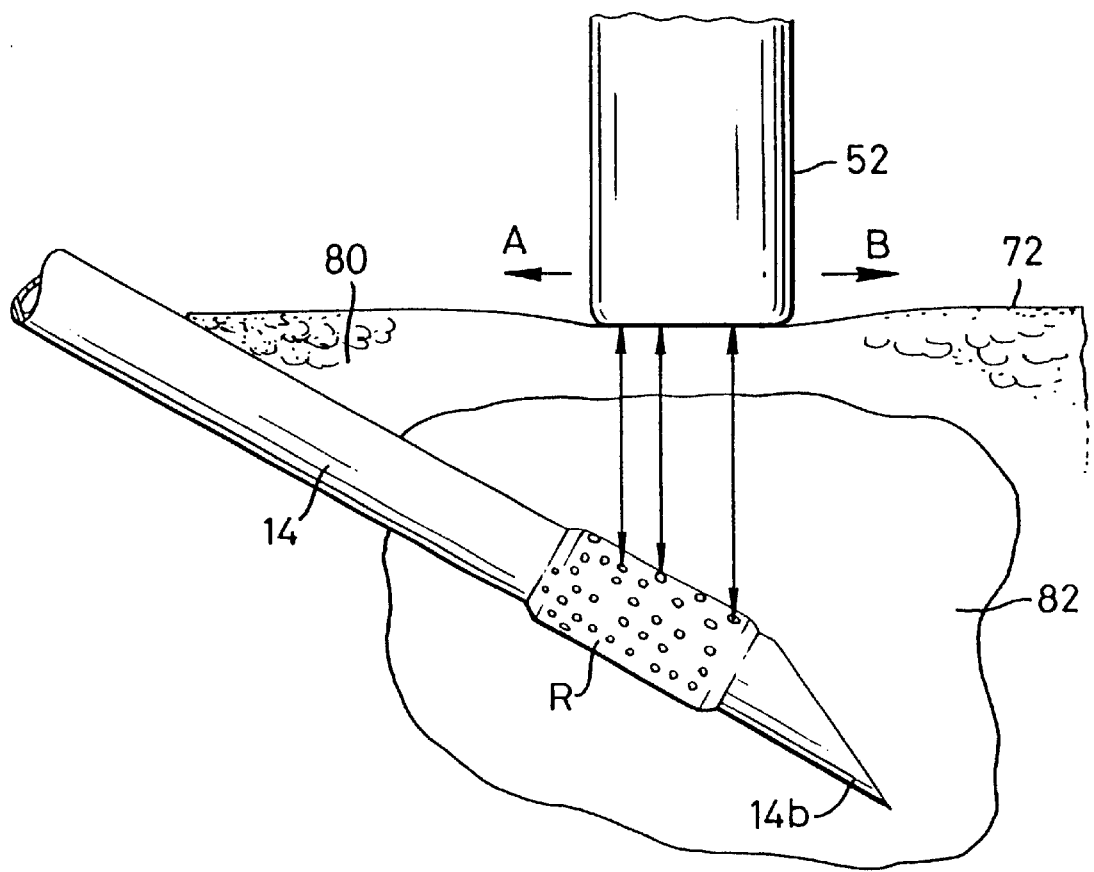
FIG. 7 is a schematic illustration of the present inventions and an ultrasound transducer for emitting and receiving ultrasound energy.

Whilst it will be appreciated that the present invention can be employed in any one of a number of situations in which it is desirable to determine the position of an instrument once embedded in a material, the following example is provided in order to illustrate at least one suitable situation. In the interest of brevity, this example relates solely to the arrangement employing an effervescent material. It will however be appreciated that alternative forms will be employed in a similar manner. Operation in the mode of the example is achieved by insertion of the needle 14 into, for example, human tissue 80 (FIG. 1) and then into the human organ under investigation, a portion of which is shown at 82 in FIG. 5. Once inserted, the effervescent material comes into contact with any fluid in said organ 82 and effervesces thereby to create a quantity of small gas bubbles 64 as illustrated in FIGS. 3 to 6. This step is enhanced when the carrier material 30 comprises a hydrophilic material which effectively acts to draw a small quantity of fluid from the organ tissue thereby exposing effervescent material 32 embedded therein to the action of the liquid and enhancing the effervescent effect. Alternatively, the instrument may be immersed in a bath of reactant before insertion into the material under inspection thereby to initiate the reaction in a controlled manner and with a preferred reactant. Once generated, the bubbles 64 become mobile in the sense that they migrate in random directions between different portions of the carrier material and grow in size as they do so. Once mobile the bubbles will have a tendency to migrate to the region of lowest pressure. In many applications this might well be at or near the interface with the material under inspection i.e. the outer surface 33 of the carrier material. Any bubbles generated in the FIG. 4 embodiment are, in theory, free to exit the carrier material and enter the material under inspection. However, as mentioned above there is a certain degree of resistance to such motion. In the event that a bubble does pass across the interface, it will tend to coalesce on the surface 33 before passing into the material surrounding the instrument. This is particularly the case when the surrounding material exerts pressure on the carrier material. An ultrasound transducer 52 is placed on the outer surface 72 of, for example, the patents body as shown in FIGS. 1 and 7 and acts to direct a quantity of ultrasonic energy in the general direction of the needle 14. The transducer 52 is then moved over surface 72 in the direction of arrows A, B until a reflection is detected from the highly reflective gas bubbles 64. This reflection being substantially stronger than that of any surrounding tissue can then be employed to create an ultrasound image on a video monitor 56 which is significantly stronger and better defined than is presently possible. Guidance of the instrument is conventional in that it relies on the operator to interpret the video image and move the instrument to its operating position. Clearly, this process will be made much simpler due to the improved visualisation possible with the present invention.

It will be appreciated that the present invention may be applied to a number of situations where it is desirable to enhance an ultrasonically generated video image. For example, one may employ it on a catheter, a simple needle or any other similar device either within or outside the medical field.

What is claimed is:

1. An instrument insertable into a medium and capable of being detected with ultrasonic imaging equipment comprising:
    an elongate member, for insertion into said medium and having a region the position of which it is desirable to monitor;
    bubble generating means, for generating a plurality of discrete mobile bubbles at said desired region, whereby said discrete mobile bubbles are detectable by ultrasonic imaging equipment thereby to give an accurate indication of the position of said region; and
    a coating at said region, said bubble generating means being contained within said coating thereby to generate said bubbles within said coating and release them for passage therethrough.

2. An instrument as claimed in claim 1 in which said bubble generating means comprises a reactive substance which upon interaction with a reactant acts to produce said bubbles.

3. An instrument as claimed in claim 1 which said bubble generating means comprises an effervescent material which, upon contacting fluid effervesces thereby to create said bubbles.

4. An instrument as claimed in claim 3 in which said effervescent material comprises a mixture of sodium hydrogen carbonate and citric powder.

5. An instrument as claimed in claim 1 further including an outer layer of fluid permeable-gas impermeable material for allowing fluid to enter the coating and retaining any gas bubbles created therein within said coating.

6. An instrument as claimed in claim 1 in which the coating comprises a fluid permeable-gas impermeable polymer.

7. An instrument as claimed in claim 1 including an outer gas impermeable layer and a plurality of openings for allowing fluid to contact the reactant but limiting the escape of any gas bubbles from the carrier material.

8. An instrument as claimed in claim 1 in which said coating comprises a matrix of interconnecting passages having a pore size through which fluid may permeate but in which gas bubbles of a size larger than a predetermined size are retained.

9. An instrument as claimed in claim 1 in which the coating comprises a hydrophilic material.

10. An instrument as claimed in claim 1 in which said coating forms a carrier material throughout which said bubble generating means is dispensed.

11. An instrument as claimed in claim 1 in which the coating comprises an epoxy based resin.

12. An instrument as claimed in claim 11 in which the coating comprises EPOTEC epoxy 353 ND resin.

13. An instrument as claimed in claim 1 in which said instrument includes a distal end and said coating lies adjacent said distal end.

14. An instrument as claimed in claim 1 in which said coating is provided at a plurality of discrete positions along said elongate member.

15. An instrument as claimed in claim 1 in which said elongate member comprises a biopsy needle assembly.

16. A method of determining the position of an instrument insertable into a medium and capable of being detected with ultrasonic imaging equipment comprising an elongate member for insertion into said medium and having a region the position of which it is desirable to monitor, bubble generating means for generating a plurality of discrete mobile bubbles at said desired region, and a coating at said region, said bubble generating means being contained within said coating thereby to generate said bubbles within said coating and release them for passage therethrough, the discrete mobile bubbles being detectable by ultrasonic imaging equipment thereby to give an accurate indication of the position of said region;

said method including the steps of:
(a) inserting said instrument into a medium;
(b) creating said plurality of discrete mobile bubbles at said desired region;
(c) positioning an ultrasound transducer on a surface of the medium and transmitting an ultrasonic signal in a direction substantially towards said instrument thereby to cause at least some of said signals to be reflected by said bubbles and collecting said reflected signal in said transducer;
(d) converting the reflected ultrasound signal into an electrical signal suitable for creating a display on a video monitor; and
(e) displaying a video image from said signal, thereby to provide a visual representation of the position of said instrument.

17. An instrument insertable into a medium and capable of being detected with ultrasonic imaging equipment comprising:
an elongate member, for insertion into said medium and having a region the position of which it is desirable to monitor;
bubble generating means, for generating a plurality of discrete mobile bubbles at said desired region, said bubble generating means comprising a reactive substance which upon interaction with a reactant acts to produce said discrete mobile bubbles, whereby said discrete mobile bubbles are detectable by ultrasonic imaging equipment thereby to give an accurate indication of the position of said region.

18. An instrument insertable into a medium and capable of being detected with ultrasonic imaging equipment comprising:
an elongate member, for insertion into said medium and having a region the position of which it is desirable to monitor;
bubble generating means, for generating a plurality of discrete mobile bubbles at said desired region, said bubble generating means comprising an effervescent material which, upon contacting fluid, effervesces thereby to create said discrete mobile bubbles, whereby said discrete mobile bubbles are detectable by ultrasonic imaging equipment thereby to give an accurate indication of the position of said region.

19. An instrument as claimed in claim 17 further including a coating at said region, said bubble generating means being contained within said coating thereby to generate said bubbles within said coating and release them for passage therethrough.

20. An instrument as claimed in claim 18 further including a coating at said region, said bubble generating means being contained within said coating thereby to generate said bubbles within said coating and release them for passage therethrough.

21. An instrument as claimed in claim 18 in which said bubble generating means comprises a reactive substance which upon interaction with a reactant acts to produce said discrete mobile bubbles.

22. An instrument as claimed in claim 17 in which said bubble generating means said bubble generating means comprises an effervescent material which, upon contacting fluid, effervesces thereby to create said discrete mobile bubbles.

23. Method of conducting an investigation of a desired region in a human being, comprising the steps of:
inserting into a human being in said desired region to create a plurality of bubbles an instrument capable of being detected with ultrasonic imaging equipment comprising an elongate member suitable for insertion into said human being and having a region the position of which it is desirable to monitor, bubble generating means for generating a plurality of discrete mobile bubbles at said desired region, whereby said discrete mobile bubbles are detectable by ultrasonic imaging equipment thereby to give an accurate indication of the position of said region; and a coating at said region, said bubble generating means being contained within said coating thereby to generate said bubbles within said coating and release them for passage therethrough;
positioning an ultrasound transducer on a surface of said human being and transmitting an ultrasonic signal in a direction substantially towards said instrument, thereby to cause at least some of said signals to be reflected by said bubbles and collecting said reflected signal in said transducer;
converting the reflected ultrasound signal into an electrical signal suitable for creating a display on a video monitor; and
displaying a video image from said signal thereby to provide a visual representation of the position of the instrument.

24. Method of conducting an investigation of a desired region in a human being, comprising the steps of:
inserting into a human being in said desired region to create a plurality of bubbles an instrument capable of being detected with ultrasonic imaging equipment comprising an elongate member suitable for insertion into a human being and having a region the position of which it is desirable to monitor, bubble generating means for generating a plurality of discrete mobile bubbles at said desired region, said bubble generating means comprising a reactive substance which upon interaction with a reactant acts to produce said discrete mobile bubbles, whereby said discrete mobile bubbles are detectable by ultrasonic imaging equipment thereby to give an accurate indication of the position of said region;

positioning an ultrasound transducer on a surface of said human and transmitting an ultrasonic signal in a direction substantially towards said instrument, thereby to cause at least some of said signals to be reflected by said bubbles and collecting said reflected signal in said transducer;

converting the reflected ultrasound signal into an electrical signal suitable for creating a display on a video monitor; and displaying a video image from said signal thereby to provide a visual representation of the position of the instrument.

25. Method of conducting an investigation of a desired region in a human being, comprising the steps of:

inserting into a human being in said desired region to create a plurality of bubbles an instrument capable of being detected with ultrasonic imaging equipment comprising an elongate member suitable for insertion into said human being medium and having a region the position of which it is desirable to monitor, bubble generating means for generating a plurality of discrete mobile bubbles at said desired region, said bubble generating means comprising an effervescent material which, upon contacting fluid, effervesces thereby to create said discrete mobile bubbles, whereby said discrete mobile bubbles are detectable by ultrasonic imaging equipment thereby to give an accurate indication of the position of said region;

positioning an ultrasound transducer on a surface of said human and transmitting an ultrasonic signal in a direction substantially towards said instrument, thereby to cause at least some of said signals to be reflected by said bubbles and collecting said reflected signal in said transducer;

converting the reflected ultrasound signal into an electrical signal suitable for creating a display on a video monitor; and displaying a video image from said signal thereby to provide a visual representation of the position of the instrument.

* * * * *